United States Patent [19]  [11] 4,064,186
Gibson et al.  [45] Dec. 20, 1977

[54] HYDROGENATION OF STYRENE OXIDE TO PRODUCE 2-PHENYLETHANOL

[75] Inventors: Charles Arnold Gibson, South Charleston; Louis Foster Theiling, Jr., Charleston, both of W. Va.

[73] Assignee: Union Carbide Corporation, New York, N.Y.

[21] Appl. No.: 616,024

[22] Filed: Sept. 23, 1975

[51] Int. Cl.$^2$ ............................................. C07C 29/04
[52] U.S. Cl. ................................ 260/618 H; 260/599
[58] Field of Search ........................... 260/618 H, 632

[56] References Cited

U.S. PATENT DOCUMENTS

| | | | |
|---|---|---|---|
| 1,787,205 | 12/1930 | Loehr | 260/618 H |
| 2,524,096 | 10/1950 | Wood | 260/618 H |
| 2,822,403 | 2/1958 | Hopff et al. | 260/618 H |
| 3,579,593 | 5/1971 | Wood | 260/618 H |

FOREIGN PATENT DOCUMENTS

| | | | |
|---|---|---|---|
| 512,236 | 4/1955 | Canada | 260/618 H |

OTHER PUBLICATIONS

Sokol'skii et al, Chem. Abst., vol. 69, No. 2660p, 1970.

*Primary Examiner*—James O. Thomas, Jr.
*Assistant Examiner*—James H. Reamer
*Attorney, Agent, or Firm*—Bernard Francis Crowe

[57] ABSTRACT

Styrene oxide is hydrogenated in the presence of a hydrogenation catalyst to produce 2-phenylethanol. The proportion of unreacted styrene oxide in the reaction mixture is carefully controlled in order to avoid the production of undesired by-products.

5 Claims, No Drawings

HYDROGENATION OF STYRENE OXIDE TO PRODUCE 2-PHENYLETHANOL

The invention relates to the production of 2-phenylethanol by the hydrogenation of styrene oxide.

2-Phenylethanol is a valuable article of commerce that is employed, for instance, in the perfume industry. It has a rose or floral odor that makes it highly desirable for use in both high quality perfumes and in fragrances that are added to soaps and detergents. The principal commercial method for its production in the past has been the Friedel-Crafts reaction of benzene with ethylene oxide. A major disadvantage of this process is the fact that the Friedel-Crafts catalysts are corrosive, which necessitates the use of expensive, corrosion resistance equipment.

The preparation of 2-phenylethanol by the hydrogenation of styrene oxide has also been studied extensively, but apparently it has not been employed in the commercial preparation of 2-phenylethanol. The following patents disclose the production of 2-phenylethanol by the hydrogenation of styrene oxide in the liquid phase: Wood, U.S. Pat. No. 2,524,096; Hopff et al., U.S. Pat. No. 2,822, 403; U.S. Rubber Co., British Pat. Spec. No. 678,589; and Frisch, Canadian Pat. No. 512, 236.

With two exceptions, noted below, the hydrogenation reactions disclosed in each of these patents appear to be limited to batch processes wherein the full charge of styrene oxide is in contact with all of the hydrogenation catalyst and either all or most of the hydrogen, from the beginning of the reaction. In the cited British patent, while it is stated that the reaction is usually carried out as a batch process, at page 2, lines 71 et seq., it is said that the reaction can be "conducted continuously, for example by continuously supplying a liquid mixture of styrene oxide and hydrogenation catalyst, with a solvent and with or without an alkaline-reacting material to suppress catalytic [sic] poisioning, to a reaction zone where it is intimately mixed with hydrogen gas..., continuously withdrawing the reaction mixture from the reacting zone at a rate equivalent to that of the incoming reaction mixture,...".* In such a case, the reacting zone would contain an equilibrium mixture which would contain relatively high proportions of styrene oxide. In carrying out a continuous process as taught in the British patent, it would be expected that up to about 10 percent of the styrene oxide would fail to react, and perhaps about 5 percent of the styrene oxide would be converted to high molecular weight condensation products and other undesired by-products.

*An equivalent disclosure is found in Frisch.

The present invention is an improvement in the process wherein styrene oxide is hydrogenated to produce 2-phenylethanol. In accordance with the invention, styrene oxide is introduced into a reaction mixture containing diluent, hydrogenation catalyst, and hydrogen, said reaction mixture being maintained at a temperature and pressure sufficient to enable the styrene oxide to react with said hydrogen to produce 2-phenylethanol, wherein the rate that said styrene oxide is introduced into said reaction mixture is controlled so that at no time during the process will the concentration of styrene oxide in the reaction mixture exceed about 0.2 weight percent, the percentage being based upon weight of liquid reaction mixture. The principal advantage obtained by practicing the invention is that very low proportions of undesired by-products are produced. Normally, the resinous by-products produced in a reaction of this type would deactivate the catalyst by coating the surface. Therefore, unless the catalyst is washed between runs to remove these by-products, it loses its activity rapidly. With the present invention, however, the amount of resinous by-products is so low that the catalyst can be used for many, many runs without washing between runs.

The process of the invention can be described as a semi-batch reaction wherein all of the components of the reaction mixture except the styrene oxide are initially charged to a convenient reaction vessel. The reaction is then carried out by continuously feeding styrene oxide to the reaction mixture at such a rate that the proportion of unreacted styrene oxide in the reaction mixture does not exceed about 0.2 weight percent, based upon the weight of liquid reaction mixture. The initial reaction mixture will contain a diluent that is a solvent for both the styrene oxide reactant and the 2-phenylethanol product, hydrogenation catalyst, and preferably a base for maintaining the reaction mixture at a pH of about 7 to 8. The reaction mixture should be contained in a closed vessel that is capable of maintaining the requisite hydrogen pressure on the reaction mixture.

The process is carried out at a temperature sufficient to hydrogenate the styrene oxide to produce 2-phenylethanol. While the hydrogenation will occur at low temperatures, for instance, 25° to 50° C., it is preferable to carry out the hydrogenation at higher temperatures in order to faciliate removal of the exothermic heat of reaction, which is 45 kilocalories per mole. Thus, broadly, temperatures within the range of about 50° to about 120° C., and preferably from about 80° to about 100° C., are employed. At this temperature, rapid hydrogenation of styrene oxide occurs with little or no side reactions. It has been found that best results are obtained if the reaction mixture is brought to the desired reaction temperature prior to the start of the styrene oxide feed. Thereafter, the reaction temperature is maintained by using a mixture of heating and cooling water, as required.

The pressure of hydrogen in the reaction vessel will normally be at least about 250 p.s.i.g., preferably at least 400 to 600 p.s.i.g., and more preferably about 1200 p.s.i.g. While the process would be operable at pressure higher than 1200 p.s.i.g., little advantage has been found in operating at such higher pressures.

The effective volume of the reactor to be used in the process of the invention will depend upon specific design features and the degree of mixing that the reactor could provide. As an approximation, the initial hydrogenation should be carried out using approximately 40 percent free space in the reactor. That is, at the end of the styrene oxide feed, there would be approximately 40 percent free space in the reactor.

The reaction employs a diluent that is a solvent for both the styrene oxide and the 2-phenylethanol. The diluent should also be substantially unreactive with styrene oxide under the conditions of the reaction. Isopropyl alcohol has been found to be an effective diluent, although other organic solvents can be employed. Such other solvents include 2-butanol, benzene, toluene, xylene, and the like. Solvents containing ether and carbonyl groups should be avoided. Methanol, ethanol, n-propyl alcohol and n-butyl alcohol can be used, but they may yield slightly more by-products than secondary alcohols because of their greater reactivity. The solvent is usually used in amounts of from about 15 to about 30, and preferably from about 20 to about 25, weight percent, based on weight of final reaction mixture.

It is desirable to maintain the reaction mixture at an almost neutral pH, i.e., at a pH of about 7 to 8. For this purpose, a small amount of water and an alkaline material such as sodium carbonate can be added to the reaction mixture. The water does not react with the styrene oxide under the conditions of the reactions, but is used to facilitate the solubility of the alkaline material in the reaction mixture. About 0.5 weight percent of sodium carbonate, and about 0.8 to 0.9 weight percent water (including any water that might be added with the catalyst), are usually employed, the percentages being based on weight of the final reaction mixture. As is known in the art, by maintaining the pH about neutral, the isomerization of styrene oxide to phenylacetaldehyde is avoided, aldol reactions are avoided, and the reaction of water with styrene oxide is avoided. The reason that a base is required to maintain the desired pH, is that the trace impurities ordinarily encountered in styrene oxide are acidic.

The hydrogen that is employed in the reaction should be free of catalyst poisons such as carbon monoxide, chlorides, and sulfur. Also, the hydrogen should not contain more than a trace amount of low molecular weight hydrocarbons. Regardless of the hydrogen purity, the reaction vessel should be purged with hydrogen prior to the start up of the reaction. The purge is necessary for safety reasons (to exclude oxygen from the reaction zone), as well as to reduce side reactions. It is preferred to add hydrogen continuously during the reaction as it is used up, although it can be added batchwise, if desired.

A hydrogenation catalyst is employed in the process. These include nickel, palladium, platinum, and the like. Raney nickel is the preferred catalyst. Normally, Raney nickel is stored in water with a discrete layer of water as a protective covering. Before the Raney nickel is charged to the reactor, the excess water is preferably decanted. The remaining slurry remains about 63 percent Raney nickel and 37 percent water, by weight. This mixture of Raney nickel and water is referred to as Raney nickel sludge. Nickel is preferred as the catalyst when the styrene oxide feed contains phenylacetaldehyde as an impurity, since the nickel will catalyze the hydrogenation of this aldehyde to the desired 2phenylethanol product. Palladium and platinum will not do this, although with very pure styrene oxide they are as good as nickel, except for cost.

The catalyst is used in catalytically significant amounts. For instance, catalyst proportions of from about 0.8 to about 2.3, and preferably about 1.4, weight percent, based on total styrene oxide feed, have been found acceptable.

The major novelty of this invention resides in controlling the concentration of unreacted styrene oxide in the reaction mixture at less than about 0.2 l weight percent of the liquid mixture. This is done by controlling the rate of feed of the styrene oxide into the reaction mixture so that the concentration of unreacted styrene oxide at all times during the course of the reaction is below 0.2 weight percent. Thus, at any point in the reaction, the styrene oxide content should be less than 0.2 weight percent of the solvent plus contained 2-phenylethanol, i.e., the 2-phenylethanol produced up to that point. The concentration of styrene oxide at any point during the reaction can be determined by removing a sample, cooling it to room temperature, and analyzing it by conventional procedures. The act of removing a sample from the reaction mixture will immediately stop the reaction in that sample because hydrogen is no longer present.

An even, continuous styrene oxide feed rate is preferred. That feed rate which will yield the desired unreacted styrene oxide content for any particular size batch will have to be determined experimentally. The Examples, below, illustrate feed rates that have been found useful for the batch sizes indicated.

After all of the styrene oxide has been fed to the reaction mixture, it is preferred to continue the hydrogenation reaction for a period of time, for instance, from about ½ hour to about 1 hour, in order to improve the quality of the final hydrogenation mixture. The extra reaction time insures conversion of all the styrene oxide fed, and when nickel is the catalyst, effects conversion of all phenylacetaldehyde present to 2-phenylethanol.

At the conclusion of the reaction, the 2-phenylethanol product is recovered by conventional procedures, as is illustrated below in Example 1.

The following Examples illustrate the practice of the invention:

EXAMPLE 1

Reaction Part 1

Anhydrous isopropyl alcohol, 812 grams, sodium carbonate, 17.5 grams, water, 7 grams, and Raney Nickel sludge, 61.5 l grams, were charged to a stirred pressure vessel of 1.84 gallons total capacity. The autoclave was purged with hydrogen to remove inert gases and heated to 80° C. The system was pressurized to 1200 p.s.i.g. with a continuous hydrogen feed. The hydrogenation vessel is purged with a volume of hydrogen approximately three times its total displaced volume per hour. In the event a continuous purge cannot be accommodated, the hydrogenation vessel should be vented to atmospheric pressure and again pressurized after the termination of the styrene oxide feed. Styrene oxide, 2680 grams, was fed at a uniform rate to the hydrogenator over a 5-hour period. Agitation in the vessel must be sufficient to maintain the catalyst in suspension. The reaction conditions were maintained for one additional hour, after which the vessel was cooled to 30° C. and vented to atmospheric pressure. At this point, the reaction mixture may be filtered to remove catalyst and any undissolved sodium carbonate prior to further processing by distillation.

The following process description describes the recycle of Raney Nickel catalyst to subsequent hydrogenation without complete isolation. The reaction mixture 3508 grams, was discharged to a calibrated vessel. The reaction mixture settled completely in 3 hours at ambient temperature. The catalyst and undissolved sodium carbonate settles from the hydrogenation mixture in about 30 minutes at 90° C. A total of 240 grams, 211 milliliters, of the settled reaction mixture, which contained the Raney Nickel and undissolved sodium carbonate, was removed after 3268 grams of hydrogenation mixture had been decanted. In addition to the Raney Nickel and undissolved sodium carbonate, the 240 grams of settled hydrogenation mixture contained 47.5 grams of isopropyl alcohol, 137 grams of 2-phenylethanol, 3.6 grams of water, and trace amounts of organic compounds which will be discussed later. The decanted hydrogenation mixture, 3268 grams, analyzed 72.5 weight percent 2-phenylethanol. This is equivalent to a yield of 95.5 percent based on the styrene oxide taken at 100 percent purity.

Part 2

The 240 grams of settled hydrogenation mixture from the first run was charged to the autoclave with 764.5 grams of isopropyl alcohol, 17.5 grams of sodium carbonate, and 32 grams of water. To make up for losses, a small amount, e.g., up to about 10 percent of the total amount of catalyst used, of fresh catalyst may have to be added to each run. After purging the hydrogenation vessel with hydrogen, the system was heated to 80° C. and pressurized to 1200 p.s.i.g. A total of 2543 grams of styrene oxide was fed at a uniform rate to the stirred vessel over a 5-hour period. The hydrogenation system was maintained at normal operating conditions for an additional hour. The decantation procedure as practiced in the initial hydrogenation was repeated. The settled bottom (240 grams, 211 milliliters) was removed and recharged to the hydrogenation vessel for a subsequent run. The decanted reaction mixture, 3290 grams, was analyzed by gas chromatography. The mixture assayed 76.5 weight percent of 2-phenylethanol which is essentially a quantitative yield based on styrene oxide and 2-phenylethanol introduced in the second hydrogenation.

A third hydrogenation was made using the exact charge and procedures employed for the second run. There was a 5-day delay between the second and third runs. During this period, the hydrogenation vessel was held under hydrogen pressure. The portion of the second reaction mixture which contained the Raney Nickel was stored at ambient temperature without additional precaution. Analysis of the hydrogenated mixture, 3551 grams, afforded 72.3 weight percent 2;1-phenylethanol. This is equivalent to a 95 percent yield of 2-phenylethanol based on the styrene oxide with an assumed purity of 100 percent.

Isolation

The reaction products from the three hydrogenations were filtered and combined. To this point, sampling and losses during transfers amount to 292 grams or 220 grams of crude 2-phenylethanol. The combined hydrogenation mixture, 9926 grams, was placed on a one-tray-distillation apparatus and the solvent, isopropyl alcohol with a small amount of ethyl benzene, was removed to a kettle temperature of 120° C. at 10 mm. Hg pressure. A total of 7460 grams of crude product was removed from the evaporator. After correction for the initial losses, the crude product weight was 7680 grams. Gas chromatographic analysis of the crude product using an internal standard procedure gave a purity of 97.5 weight percent 2-phenylethanol. This is equivalent to a yield of 95 percent 2-phenylethanol based on styrene oxide with a purity of 100 percent. Based on the actual purity of styrene oxide, the yield is in excess of 97 percent.

Refining of Crude 2-Phenylethanol

Crude 2-phenylethanol which assayed 97.5 weight percent was distilled on a 15-tray Oldershaw column. The recovery of refined product, 99 percent purity, was 95-percent based on the contained 2-phenylethanol. The refined 2-phenylethanol contained 0.7 percent 1phenyl-1propanol and 0.2 percent of methyl phenyl carbinol. Additional analyses were made using a gas chromatograph interfaced with a high resolution mass spectrometer. Trace quantities of methyl CELLOSOLVE acetate, bis(2-methoxyethyl) ether, 2-ethylhexanol, and 2-ethylhexyl acetate were identified in the forefraction. Benzyl alcohol was identified as part of the peak which had been shown as 1-phenyl-1-propanol by the gas chromatographic procedure discussed above.

The foregoing Example illustrates one of the desirable features of the invention, namely, the ability to recycle the catalyst without isolation between runs. It also illustrates the high conversion rate to the desired product, and lack of appreciable amounts of by-products, that can be obtained by the practice of the invention.

EXAMPLE 2

The following Table displays the reaction conditions and yields that were obtained in several different runs, using the general procedure described above in Example 1.

TABLE I

| | | | | | | | | | | |
|---|---|---|---|---|---|---|---|---|---|---|
| | | | | 2-PHENYLETHANOL PREPARATION FROM SYTRENE OXIDE | | | | | | |
| Run No. | Reactor Volume | Reactor Temperature °C. | Reactor $H_2$ Pressure | Styrene Oxide gms | Feed Time Hours | Additional Reaction Time (hrs) | Isopropanol gms | Raney (b) Nickel (gms) Dry Wt. | Water (c) gms | Sodium Carbonate $Na_2CO_3$ gms | 2-Phenyl-Ethanol Yield % |
| 1 (a) | 1.84 gal. | 80–85 | 1200 | 2680 | 5 | 1 | 812 | 39 | 7.0 | 17.5 | 98 |
| 2 | 2 liters | 70–80 | 400–500 | 765 | 5 | 1 | 232 | 11 | 2.0 | 5.0 | 95 |
| 3 | 2 liters | 85–100 | 400 | 765 | 5 | 1 | 232 | 11 | 2.0 | 5.0 | 97.5 |
| 4 | 2 liters | 75–80 | 300 | 765 | 5 | 1 | 232 | 11 | 2.0 | 5.0 | 94 |
| 5 | 2 liters | 75–80 | 150 | 765 | 5 | 1 | 232 | 11 | 2.0 | 5.0 | 43 |
| 6 | 2 liters | 85–90 | 250 | 765 | 5 | 1 | 232 | 11 | 2.0 | 5.0 | 93 |

(a) First part of 3 part run described in Example 1.
(b) Raney Nickel added as a slurry 63% wt. Raney Nickel and 37% water.
(c) In addition to the water added with the catalyst.

EXAMPLE 3

Preparation of 2-Phenylethanol Using Palladium Catalyst

Anhydrous isopropyl alcohol, 406 grams, aqueous potassium hydroxide, 60 grams of a 4 percent solution, and 1 gram of 3 percent palladium on carbon were charged to a 2-liter stainless steel autoclave. The autoclave was purged with hydrogen and heated to 85° C. The autoclave was pressurized to 1200 p.s.i.g. with hydrogen. Styrene oxide, 765 grams of 97 percent purity, was fed to the stirred autoclave over a 7-hour period at a uniform rate. Hydrogen pressure was maintained at 1100 to 1200 p.s.i.g. by alternately adding fresh hydrogen. Immediately after the adddition of styrene oxide, the reaction mixture was cooled to ambient temperature and analyzed by gas chromatography using an internal standard. The yield 2-phenylethanol was 92.2 percent based on a styrene oxide purity of 97.0 percent.

The unrefined reaction mixture contained 1.12 1 weight percent phenylacetaldehyde and 0.7 weight percent phenylpropanol-2. A portion of the reaction mixture, 1060 grams, was distilled to give 580 grams of 97.8 percent 2-phenylethanol. This is equivalent to 88.16 percent of the theoretical 2-phenylethanol and a recovery efficiency based on the gas chromatographic analysis of the unrefined product of 95.62 percent.

The styrene oxide contents of the reaction mixtures of Examples 1–3 were analyzed at various times during each reaction. The results are displayed below in Table II.

TABLE II

HYDROGENATION OF STYRENE OXIDE TO 2-PHENYLETHANOL; RESIDUAL STYRENE OXIDE CONCENTRATIONS IN INTERMEDIATE REACTION SAMPLES

| Example Number | Reactor Samples Time In Hours from Initiation | Styrene Oxide, Percent |
|---|---|---|
| 1-Part 1 | 2 | 0.15 |
|  | 4 | 0.37 |
|  | 5 | 0.11 |
|  | 6 | nil |
|  | Final Product | nil |
| 1-Part 2 | 2 | 0.14 |
|  | 4 | 0.32 |
|  | 5 | 0.46 |
|  | 6 | 0.03 |
|  | Final Product | nil |
| 1-Part 3 | 2 | 0.104 |
|  | 4 | 0.99 |
|  | 5 | 1.51 |
|  | 6 | 0.04 |
|  | Final Product | nil |
| 2-Run 2 | 2 | 0.05 |
|  | 4 | 0.14 |
|  | 5 | 0.08 |
|  | 6 | 0.03 |
|  | Final Product | nil |
| 2-Run 3 | 2 | 0.08 |
|  | 4 | 0.04 |
|  | 5 | 0.183 |
|  | 6 | 0.06 |
|  | Final Product | nil |
| 2-Run 4 | 2 | 0.02 |
|  | 4 | 0.15 |
|  | 5 | 0.18 |
|  | 6 | 0.24 |
|  | Final Product | nil |
| 2-Run 5 | 2 | 13.6 |
|  | 4 | 17.8 |
|  | 5 | 21.4 |
|  | 6 | 36.7 |
|  | Final Product | 27.5 |
| 2-Run 6 | 2 | 0.175 |
|  | 4 | 0.147 |
|  | 5 | 1.38 |
|  | 6 | 0.06 |
|  | Final Product | nil |
|  | 2 | nil |
|  | 4 | nil |
|  | 6 | nil |
|  | Final Product | 0.7 |

The styrene oxide analyses reported herein were done by gas chromatography. The percentage of styrene oxide is based upon the weight of solvent plus contained product.

Control 1

Batch Preparation of 2-Phenylethanol From Styrene Oxide Using Raney Nickel

A 2-liter stirred autoclave was purged with hydrogen at atmospheric pressure. Styrene oxide (765 grams, 6.375 moles), 232 grams of isopropyl alcohol, 5.0 grams of sodium carbonate, 7.0 grams of water, and 17.5 grams of Raney Nickel sludge was charged to the autoclave. The 17.5 grams of Raney nickel sludge contained 11 grams of nickel and 6.5 grams of water. The stirred mixture was heated to 80° C. and hydrogen pressure was increased gradually to 400 p.s.i.g. over a 1-hour period. The pressure was further increased to 600 p.s.i.g over a 45 minute period. A gradual increase of the hydrogen pressure in the reaction vessel was necessary to prevent overheating and exceeding 80° C. The reaction was continued for 3 ½ hours until no evidence of hydrogen consumption could be detected at 600 p.s.i.g. The liquid portion of the hydrogenation mixture was 1016 grams. Analysis of the crude reaction product using gas chromatography showed 65.63 percent 2-phenylethanol and 0.61 percent unreacted styrene oxide. The yield of 2-phenylethanol was 85.73 percent, 5.466 moles, based on the total charge of styrene oxide. The unreacted styrene oxide was 6.2 grams or 0.051 moles. The crude reaction mixture was filtered and flash distilled on a one tray evaporator. A total of 660 grams, 5.41 moles, of 2-phenylethanol was isolated at a vapor temperature of 86° C. at 4.5 millimeter mercury pressure.

Control 2

Batch Preparation of 2-Phenylethanol From Styrene Oxide Using Palladium

A 2-liter stirred autoclave was purged with hydrogen at atmospheric pressure. Styrene oxide (765 grams, 6.375 moles), 232 grams of isopropyl alcohol, 5.0 grams of sodium carbonate, 10.0 1 grams of water, and 3.0 grams of 3 percent palladium on carbon was charged to the autoclave. The stirred mixture was heated to 80° C. and hydrogen pressure was slowly increased to 300 p.s.i.g. over a 90 minute period. The pressure was maintained at 300 p.s.i.g. for an additional period of 35 minutes at which time the consumption of hydrogen had essentially stopped. The hydrogenated mixture, 1004 grams, was cooled and removed from the stirred autoclave. The hydrogenated mixture assayed 33.68 percent 2-phenylethanol and 13.69 percent styrene oxide. Based on the initial weight of styrene oxide, the yield of 2-phenylethanol was 43.95 percent and the efficiency based on recoverable styrene oxide was 53.67 percent. The filtered reaction mixture was flash distilled on a one tray evaporator. A fraction, 557 grams, was removed at a vapor temperature of 89° C. at 5 mm. Hg pressure. The distilled fraction contained 65.95 percent 2-phenylethanol. A total of 202 grams of high boiling residues remained in the distillation apparatus after removing the styrene oxide and 2-phenylethanol.

EXAMPLE 4

Semi-Batch Preparation of 2-Phenylethanol From Styrene Oxide Using Palladium

A 2-liter, stirred autoclave was purged with hydrogen. Isopropyl alcohol, 232 grams, water, 10 grams, sodium carbonate, 5.0 grams, and 3.0 grams of 3 percent palladium were charged to the autoclave. The stirred mixture was heated to 100° C. and pressurized to 1200 p.s.i.g. with hydrogen. Styrene oxide, 765 grams, 6.375 moles, was fed to the autoclave over a 5 hour period. The hydrogen pressure was maintained at 1200 p.s.i.g. and the reaction mixture was stirred at 100° C. for an additional hour. The contents of the autoclave, 1069 grams, was cooled and discharged. The crude reaction mixture assayed 66.87 percent 2-phenylethanol which was equivalent to a yield of 91.91 percent based on the styrene oxide initially fed to the autoclave. The crude reaction mixture was filtered and flash distilled on a one tray evaporator. A 723 gram fraction was removed at 73° C. and 2.5 mm. Hg pressure. A total of 71 grams of residue remained in the distillation apparatus. The distillate assayed 94.28 percent 2-phenylethanol, 0.14 percent styrene oxide, and 1.78 percent phenylacetaldehyde.

Control 3

Continuous Preparation of 2-Phenylethanol From Styrene Oxide Using Raney Nickel in Isopropyl Alcohol Solvent A 2-liter stirred autoclave was purged with hydrogen and charged with 200 grams of isopropyl alcohol, 7 grams of water, and 15 grams of sodium carbonate. The stirred mixture was heated to 100° C. and the autoclave was pressurized to 600 p.s.i.g. with a continuous feed of hydrogen. A mixture of styrene oxide (1530 grams, 12.5 moles), isopropyl alcohol, 464 grams, water, 14 grams, and 35 grams of Raney Nickel sludge was fed continuously to the autoclave over a period of 4½ hours. After the feed had been commenced for 2 hours, reaction product was removed continuously from the autoclave at an average rate of 217 grams per 30 minute period. The product removal was terminated at the conclusion of the feed period and the reactor contents were cooled to ambient temperature. A total of 1085 grams of reaction product was made continuously and an additional 1047 grams of reaction mixture was removed from the autoclave after terminating the hydrogenation. Analyses of the reactor effluent for each 30 minute period and the final reactor compositions (in weight percent) are summarized in the following table.

TABLE III

| Fraction | Isopropyl Alcohol | Ethyl Benzene | Styrene Oxide | Phenyl-Acetaldehyde | 1-Phenyl-1 Propanol | 2-Phenyl-Ethanol |
|---|---|---|---|---|---|---|
| 1 | 32.42 | 2.49 | 29.15 | 2.28 | 0.43 | 33.23 |
| 2 | — | — | 16.69 | — | — | 45.62 |
| 3 | — | — | 13.96 | — | — | 49.92 |
| 4 | — | — | 8.01 | — | — | 56.66 |
| 5 | 30.37 | 3.3 | 6.16 | 0.66 | 0.6 | 58.91 |
| Final Reactor Product | 31.29 | 3.3 | 2.90 | 0.66 | 0.63 | 61.22 |

Control 4

Continuous Preparation of 2-Phenylethanol From Styrene Oxide Using Raney Nickel in Ethyl Alcohol Solvent A 2-liter stirred autoclave was purged with hydrogen and charged with 100 grams of ethyl alcohol. The hydrogen pressure was regulated to provide a constant pressure of 100 p.s.i.g. by means of continuous hydrogen feed. A mixture of styrene oxide, 700 grams, ethyl alcohol, 1400 grams, sodium hydroxide pellets, 23 grams, water, 23 grams, and 52.5 grams of Raney Nickel sludge was prepared in a separate container for feed to the autoclave. The Raney Nickel sludge contained 63 percent dry weight Raney Nickel and 37 percent water. The above mixture was fed to the stirred autoclave over a period of 5¼ hours and the reactor temperature was maintained at 25° to 27° C. The feed to the reactor was initiated 30 minutes prior to starting the removal of product. After the feed period was completed, the hydrogen pressure was reduced to atmospheric conditions and the reactor contents were discharged. The continuous discharge of reactor product is summarized in the following Table.

TABLE IV

| Time/hrs. | Sample Number | Product Removal Grams | Product Removal Milliliter | Comments |
|---|---|---|---|---|
| 0 | — | — | — | Initiated Feed |
| 0.5 | — | — | — | Removing Reactor Product |
| 1.5 | 1 | 423 | 500 | |
| 2.5 | 2 | 363 | 400 | |
| 3.5 | 3 | 364 | 400 | |
| 4.5 | 4 | 390 | 400 | |
| 5.25 | 5 | 265 | 300 | |
| Final Reactor Product | 6 | 426 | 505 | |

The average analysis of the above samples by gas chromatography with small deviation afforded 69 percent ethyl alcohol, 1.01 percent ethyl benzene, 1.28 percent styrene, 0.59 percent styrene oxide, 0.1 percent propyl benzene, 0.20 percent of a mixture of 1-phenyl-1-propanol and benzylalcohol, 8.17 percent 2-phenylethanol, 4.32 percent 2-phenyl-2-ethoxyethanol, and 15.39 percent 1-phenyl-2-ethoxyethanol.

What is claimed is:

1. Process for producing 2-phenylethanol by reacting styrene oxide in the liquid phase with hydrogen in a closed reaction zone and in the presence of Raney nickel hydrogenation catalyst, which process comprises introducing styrene oxide into a reaction mixture comprising an organic liquid that is a solvent for styrene oxide and 2-phenylethanol and which is substantially unreactive with styrene oxide under the conditions of the process, and a catalytically effective quantity of Raney nickel hydrogenation catalyst, at a rate such that the proportion of unreacted styrene oxide in the reaction mixture does not exceed about 0.2 weight percent, based on weight of solvent plus contained 2-phenylethanol, the reaction mixture being maintained at a temperature and hydrogen pressure sufficient to effect reaction between said styrene oxide and hydrogen to produce 2-phenylethanol, said hydrogen pressure being at least about 250 p.s.i.g.

2. The process of claim 1 wherein the reaction mixture contains sufficient alkaline material to maintain the pH of the reaction mixture between about 7 and about 8.

3. The process of claim 1 wherein the organic liquid is isopropyl alcohol.

4. The process of claim 1 wherein the temperature is within the range of from about 50° to about 120° C.

5. The process of claim 1 wherein the pressure is at least about 400 p.s.i.g.

* * * * *